United States Patent
Lown et al.

(10) Patent No.: US 7,067,155 B2
(45) Date of Patent: Jun. 27, 2006

(54) ANTI-INFLAMMATORY HUMATE COMPOSITIONS AND METHODS OF USE THEREOF

(75) Inventors: John F. Lown, Dallas, TX (US); Kevin Gill, Dallas, TX (US); Stephen J. Cutler, Roswell, GA (US); Horace G. Cutler, Watkinsville, GA (US); Stanley H. Pollock, Atlanta, GA (US)

(73) Assignee: TBNI, Inc., Dallas, TX (US)

( * ) Notice: Subject to any disclaimer, the term of this patent is extended or adjusted under 35 U.S.C. 154(b) by 0 days.

(21) Appl. No.: 10/336,484

(22) Filed: Jan. 3, 2003

(65) Prior Publication Data

US 2004/0131705 A1 Jul. 8, 2004

(51) Int. Cl.
*A61K 35/12* (2006.01)
*A61K 35/37* (2006.01)
*C09K 7/00* (2006.01)

(52) U.S. Cl. .................. 424/520; 424/537; 424/543; 424/439; 507/107; 514/866

(58) Field of Classification Search ............... 507/106, 507/107; 514/825, 886, 420, 866; 424/725, 424/439, 520, 537, 543
See application file for complete search history.

(56) References Cited

U.S. PATENT DOCUMENTS

| | | | |
|---|---|---|---|
| 3,980,778 A | 9/1976 | Ayer et al. | 424/243 |
| 4,404,198 A | 9/1983 | Kelley | 424/235 |
| 4,579,844 A | 4/1986 | Rovee et al. | 514/171 |
| 5,456,935 A * | 10/1995 | Kuhnert et al. | |
| 5,466,824 A * | 11/1995 | Regtop et al. | |
| 5,626,881 A | 5/1997 | Lown | 424/520 |

OTHER PUBLICATIONS

Iubitskaia et al., Voprosy Kurotologii, Fizioterapii I Lechebnoi Fizicheskoi Kultury (Sep.-Oct 1999), (5): 22-24, Sodium humate in the treatment of osteoarthrosis.*
Shermer C L et al. Journal of the Science of Food and Agriculture (Aug. 1998). vol. 77, No. 4, pp. 479-486. Caecal metabolites and microbial populations in chickens consuming diets containing a mined humate compound.*
natur-ele™ Information Pamphlet by Technology by Nature Industries 1 Page (Front and Back), no date.
Knauf's, "Humates and Humic Acids in Medical and Veterinary Literature" pp. 1-4, Jun. 12, 1997.

(Continued)

*Primary Examiner*—Michele Flood
(74) *Attorney, Agent, or Firm*—Baker Botts L.L.P.

(57) ABSTRACT

The invention relates to an anti-inflammatory composition containing humate, such as insoluble, granular, other insoluble, or soluble humate, particularly Menefee Humate®. The invention also includes other anti-inflammatory compositions containing humate and at least one additional anti-inflammatory agent such as indomethacin or another nonsteroidal anti-inflammatory drug. The invention includes a method of treating acute or chronic inflammation in an animal, including a human, by administering one of these compositions. A method of facilitating the therapeutic effect of a therapeutic drug in an animal by co-administering humate is also provided.

23 Claims, 5 Drawing Sheets

OTHER PUBLICATIONS

"Dr. Faust's Wujinsan" at internet address <http://www.humic.com/wujinsan.html> pp. 1-3, printed Jun. 16, 2002.

"How Do You Know You Have the Best Humate" at internet address <http://www.bioag.com/best-humate.html> pp. 1-3, printed Apr. 16, 2002.

Lotosh's "Experimental Bases and Prospects for the Use of Humic Acid Preparations fr" pp. 99-103 (Infotrieve Order No. 12647575—Article not translated), 1991.

Ye et al.'s "Studies on the anti-inflammatory properties of hong yuan peat sodium humin" Acta Academiae Medicinae Sichuan vol. 16(2) pp. 127-129 (Infotrieve Order No. 12647577—Article not translated), 1985.

Earthgreen Products Inc. 2002 Product Catalog 41 Pages, 2002.

Kuhnert et al.'s, "Pharmacological and Toxicological properties of humic acids and the way of their actions in veterinary medical therapy" Dtsch. tierärztl. Wschr. 96(1) pp. 3-10, Jan. 1989.

Lang et al. "Basic Research in Immunological Response of Laboratory Rats to Humic Acid" Arch. Exper. Vet Med. vol. 2, pp. 140-146, 1987.

Fuchs et al.'s, "Untersuchungen zur enteralen Resorption von Eisen (II) aus Huminsäure-Eisen-Komplexen beim Saugferkel mit Hilfe radiomarkierten Eisens ($^{59}$Fe)*)" Dtsch. tierärztl. Wschr. 97 pp. 208 and 209, May 5, 1990.

S.A. Visser's, "Effect of Humic Substances on Mitochondrial Respiration and Oxidative Phosphorylation" The Science of the Total Environment, 62 (1987), pp. 347-354, 1987.

Sato et al.'s, "Desmutagenic effect of humic acid" Mutation Research, vol. 162 pp. 173-178, Accepted Mar. 12, 1986.

Sato et al.'s, "Mechanism of the desmutagenic effect of humic acid" Mutation Research, vol. 176 pp. 199-204, Accepted Sep. 26, 1986.

Gau et al.'s, "Humic Acid Suppresses the LPS-Induced Expression of Cell-Surface Adhesion Proteins through the Inhibition of NF-κB Activation" Toxicology and Applied Pharmacology vol. 166 pp. 59-67, Accepted Apr. 19, 2000.

Riede et al.'s, "Humate-induced activation of human granulocytes" Virchows Archiv B Cell Pathol. vol. 60 pp. 27-34, Accepted Nov. 8, 1990.

* cited by examiner

ANTI-INFLAMMATORY HUMATE COMPOSITIONS AND METHODS OF USE THEREOF

FIELD OF THE INVENTION

The present invention relates to anti-inflammatory humate compositions and their methods of use. In particular, it relates to humate compositions containing natural humate and other anti-inflammatory chemicals. It additionally relates to the use of humate in treating inflammation either alone or in combination with other anti-inflammatory chemicals.

BACKGROUND OF THE INVENTION

Chemical studies of the composition of humates such as Menefee Humate® and leonardite have revealed that they are mainly composed of the mixed salts of acid radicals found in soil humus, a product of the decay of organic matter that contains both humic and nonhumic material. Such acid radicals are collectively termed "humic acids", having individual factions named humin, humic acid, ulmic acid and fulvic acid.

Humic acids, defined as the portion of soil humus that is soluble in alkaline solution, but insoluble in acid solution, are a form of organic matter that often is added to the soil to increase fertility. Humic acids are found in rotting vegetable matter and can be detected in the black slime of an ordinary compost pit in a home garden. They are also found in the brown organic matter of a variety of soils, as well as in peats, manure, lignite, leonardite, brown coals, and the Menefee Humate®.

The exact structure of the humic acids is unknown. However, humic acids appear to be associations of molecules forming aggregates of elongated bundles of fibers at low pH, and open flexible structures perforated by voids at high pH. These voids, of varying dimensions, trap organic or inorganic particles of appropriate electronic charge. Humic acids do not have a single unique structure, but are a mixture of intermediate chemical products resulting from the decomposition and conversion of lignin and other plant materials to hard coal. Humic acids apparently are formed by the bacterial and chemical degradation of plant tissue, but in soils they also may be formed by certain secondary processes such as polymerization of polyphenols leached by rain from surface leaf litter, and condensation of phenols, quinones, and proteins that are provided by the action of soil micro-organisms and small animals on soil carbohydrates. As a result, humic acids are best characterized in terms of their origin and soil environment, rather than in rigid terms of chemical composition or chemical properties.

The humic acids have a large cation exchange capacity and hold multivalent metallic elements, such as micronutrient elements, very strongly. The molecular weight of the humic acids range from 800 to 500,000, with the weight average molecular weight ranging from about 5,000 to about 50,000. The cation exchange capacity of the humic acids varies from about 200 to about 600 meq $CaCO_2$ per 100 grams at pH 7, depending upon the origin of the extracted acids. Humic acids are polyelectrolytes and are believed to form complexes with clay particles thus enabling humic acids to bind multivalent elements with great tenacity. When the cation exchange sites on the humic acid molecule are filled predominantly with hydrogen ions, the material, considered to be an acid, is insoluble in water. However, when the predominant cations at the exchange sites are other than hydrogen, the material is called a "humate." Humates of monovalent alkali metals or ammonia are soluble in water. Such humates are referred to as "soluble". The humates of most multivalent metals are insoluble in water. Such humates are referred to as "insoluble". The term "humate" as used herein refers to both humate as well as the humic acids found in humate.

Humate has been used for decades as plant fertilizer and as an animal food supplement because of its general ability to produce healthier animals. More recently it has been used as a dietary supplement (See U.S. Pat. No. 5,626,881.) A variety of studies have explored it effects in animals. For example, humic acids' capacity to increase uptake of iron when administered as a humic acid/iron chelate was studied by Fuchs and Kunhert (*Dtsch. tierarzti*, 97(5): 208–9 (1990)). Low molecular weight humic acids have been found to be effective at crossing mitochondrial membranes (Viser, S. A., *The Science of the Total Environment*, 62: 347–354 (1987)). Humic acids have also been shown to to absorb mutagenic chemicals and prevent their disruptive effects in bacteria (Sato, T., et al., *Mutation Research*, 162: 173–178 (1986); Sate, T., et al., *Mutation Research*, 176: 199–204 (1987)).

The effects of humate or humic acids on immune system function have also been studied. Overall, humic acids and humate have been found to stimulate immune cells or the immune response. (See Gau, R. J.,et al., *Toxicol. Appl. Pharmacol.* 166(1): 59–67 (2001); Lange, N., et al., *Arch. Exper. Vet. Med.*, 2: 140–6 (1987); Reide, U. N., et al., *Virchows Archir. B. Cell Pathol.*, 60: 27–34 (1991); and Kuhnert et al., *Dtsch. tierarztl.* 96(1): 3–10 (1989).) Thus it came as some surprise when Ye et al. (Ye, S. B., et al., *Acta Acad. Med. Sichuan* 2: 127–9 (1985)) reported that intraperitoneal injection of Hong Yuan peat-derived sodium humate reduced swelling of inflamed rat paws.

Although it is not impossible for an immune-stimulatory agent to reduce inflammation, which is partially due to immune response, agents with these properties in combination are not common. Unfortunately, direct intraperitoneal injection of large amounts of humate as described in Ye et al. is not practical for non-experimental purposes. For example, Ye et al. injected 50 mg/kg of soluble sodium humate; an equivalent amount for an adult human weighing 100 kg would be 5 g of humate. Even if the humate were solubilized in a very concentrated solution, this would require injection of an uncomfortably large volume of liquid. Additionally, although humate is generally beneficial, overly large amounts of it are actually less effective as an anti-inflammatory agent than smaller amounts and may cause other, unknown health problems.

Inflammation is signaled by redness, swelling, heat, and pain as a reaction of the body against injury or assault. A variety of chemicals have been implicated as chemical mediators of the inflammatory reaction, including histamine, serotonin, kinins, prostaglandins, platelet-activating factors, leukotrienes, and, from nerve endings, substance P. Mediators of the acute inflammatory reaction seem to play roles in one or more of increasing vascular permeability, attracting leukocytes, producing pain, local edema, and necrosis.

There are steroid and non-steroid, anti-inflammatory drugs known to the art. U.S. Pat. No. 4,579,844, inventors Rovee et al., issued Apr. 1, 1986, discloses topically treating an inflammatory condition of the skin by use of the prostaglandin synthetase inhibitor concurrently with a corticosteroid. U.S. Pat. No. 4,404,198, inventor Kelley, issued Sep. 13, 1983, discloses the topical application of a composition including phenyl salicylate to treat inflammation. U.S. Pat.

No. 3,980,778, inventors Ayer et al., issued Sep. 14, 1976, discloses asteroid for use in the topical, oral or parenteral treatment of skin and mucous membrane inflammations. Numerous other anti-inflammatory medications, ranging from aspirin, acetaminophen and ibuprofen to newer COX-2 inhibitors and ketoprofin.

The wide variety of anti-inflammatory drugs is indicative of the fact that not all drugs are suitable for every indication or each individual patient. Despite this variety, there are still a number of patients whose needs are not well-met by the available range of anti-inflammatory drugs when administered in customary fashions.

SUMMARY OF THE INVENTION

The present invention provides a novel anti-inflammatory composition including humate as well as another composition including humate with at least one other anti-inflammatory chemical. The anti-inflammatory compositions may be for oral, topical or injection administration to an animal, including a human. In an exemplary embodiment, the humate is prehistoric humate such as Menefee Humate® derived from the Menefee Geological Formation in New Mexico. Additionally, in an exemplary embodiment the humate comprises at least 50% humic acids.

When the mode of administration is oral or topical, the humate may be insoluble, granular humate, other insoluble humate, or soluble humate. When the mode of administration is by injection, the humate is preferably soluble. In an exemplary embodiment, the humate comprises between approximately 0.1% and 1.0% and, more specifically, approximately 0.5% by weight of the composition. Alternatively, the humate composition may be administered orally in such a way that between approximately 0.1% and 1.0% and, more specifically, approximately 0.5% by weight of the animal's total food intake is humate.

The humate composition may also contain at least one additional anti-inflammatory agent. In an exemplary embodiment, this second agent is a nonsteroidal anti-inflammatory drug. For example, it may be an indole derivative such as indomethacin.

The invention also includes a method of reducing inflammation in a tissue of an animal, including a human, by supplying a composition containing humate to the tissue through oral, topical or injection administration. In an exemplary embodiment, if the humate is supplied orally it may constitute approximately 0.1% and 1.0% and, more specifically, approximately 0.5% by weight of the total food consumed by the animal.

The method may also include the additional step of supplying a second anti-inflammatory agent to the tissue of an animal, including a human, through oral, topical or injection administration. In an exemplary embodiment, the dosage of the second anti-inflammatory agent is reduced as compared with the dosage that would be administered if no composition containing humate were administered. The second anti-inflammatory agent may be supplied in the composition containing humate or it may be supplied in a separate composition from that containing humate. If the second agent is supplied separately from the humate it may be supplied approximately contemporaneously with the composition containing humate using the same type of administration. In a further exemplary embodiment, the humate acts a carrier to facilitate transport of the second anti-inflammatory agent to the tissue or cell where it exerts its activity. In another exemplary embodiment, a synergistic effect between the humate and other anti-inflammatory agent occurs.

In an exemplary embodiment, the composition containing humate is supplied orally in such a manner that humate constitutes approximately 0.1% and 1.0% and, more specifically, approximately 0.5% by weight of the animal's food intake and the second anti-inflammatory composition is indomethacin administered in the amount of approximately 3 mg/kg animal. The inflammation may be acute or chronic. One example of chronic inflammation is arthritis.

The invention additionally includes a method of increasing the therapeutic effect in an animal, including a human, of a therapeutic chemical by administering the therapeutic chemical with humate. The administration of humate may be contemporaneous and in the same manner as the administration of the therapeutic chemical, such as when they are in a single composition.

In an exemplary embodiment, the humate serves as a carrier for the therapeutic chemical and facilitates its delivery to a tissue or cell of the animal where the therapeutic chemical exerts its therapeutic effect. The humate and therapeutic chemical may be administered orally, topically or by injection.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3 depicts the anti-inflammatory effects of orally administered insoluble, granular Menefee Humate® on adjuvant-induced arthritis in rats. All results are from rats which had received humate for 15 days. Solution percentages represent weight percentage of humate in powder suspension with feed mix.

FIG. 4 depicts the anti-inflammatory effects of orally administered insoluble, granular Menefee Humate® on adjuvant-induced arthritis in rats. All results are from rats which had received humate for 21 days. Solution percentages represent weight percentage of humate in powder suspension with feed mix.

DETAILED DESCRIPTION OF THE INVENTION

The present invention relates to anti-inflammatory compositions including humate, which may also contain or be co-administered with at least one other anti-inflammatory agent. The invention also includes methods of administering such compositions to animals, including humans, with inflammation.

The humate may be administered in a soluble form or in a granular, insoluble form or in other forms. In an exemplary embodiment, granular, insoluble or soluble Menefee Humate® is used. The mode of administration will depend upon the form of humate, with soluble humate preferred for intravenous (IV), intramuscular (IM) or other types of injection. Soluble humate may also be used for oral ingestion or topical application, however, insoluble, granular humate or other insoluble humate is also suitable for these purposes. The humate may be administered to an area of inflammation through injection or in topical applications. Orally administered humate may be suitable to treat inflammation anywhere in the body.

Humate may also be combined with at least one other anti-inflammatory agent. Such combination may be effected by preparing a composition containing both humate and at least one other anti-inflammatory agent or by co-administering separate compositions, for example, one containing humate and another or others containing at least one other anti-inflammatory agent. In an exemplary embodiment, if the humate and anti-inflammatory agent or agents are in separate compositions, administration is approximately contemporaneous. In another embodiment, humate is administered on a regular basis, such as daily, while the anti-inflammatory agent or agents are administered periodically, for example to treat or prevent increased inflammation.

All compositions of the present invention may be prepared in a pharmaceutically acceptable carrier. Different carriers may be required depending upon the solubility of the humate selected. The selection of an appropriate carrier will be apparent to one skilled in the art. It is known in the art that pH of the solution affects the solubility of humate and its constituent parts, such as certain humic acids.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Composition of Menefee Humate®

Menefee Humate® is a humate of prehistoric origin found in the Menefee Geological Formation of northern New Mexico. Humate differs in its chemical and physical properties depending upon the source. Menefee Humate® is one of the world's highest quality humates for other known uses. Therefore, it was selected for use in the examples that follow.

Insoluble, granular Menefee Humate® is prepared by mining then screening the humate to a desired granule size. Because this process does not chemically alter the humate, it remains insoluble. The pH of the insoluble, granular Menefee Humate® is approximately 3.4 and its composition is approximately as follows:

| | |
|---|---|
| Humic Acids | 50.00% |
| Nitrogen (N) | 1.00% |
| Potassium ($K_2O$) | <0.10% |
| Phosphate ($P_2O_5$) | <0.10% |
| Calcium (Ca) | 1.04% |
| Sulfur (S) | 0.18% |
| Magnesium (Mg) | 0.14% |
| Iron (Fe) | 0.30% |
| Manganese (Mn) | 0.0004% |
| Copper (Cu) | 0.0002% |

Other trace minerals may also be present in some samples.

Soluble Menefee Humate® is prepared by forming a solution of granular humate with water, potassium phosphate and a wetting agent. The solution is then screened and processed through a spray-dryer to obtain a water-soluble powder. This powder may be added to water to form a solution with a desired concentration. The pH of soluble Menefee Humate® is approximately 6.2 and its composition is approximately as follows:

| | |
|---|---|
| Humic Acids | 60.0% |
| Fulvic Acid | 26.0% |
| Carbon | 11.5% |
| Calcium (Ca) | 1.7% |
| Sulfur (S) | 0.4% |
| Magnesium (Mg) | 0.3% |
| Iron (Fe) | 0.06% |

Other trace minerals may also be present in some samples.

Example 2

Effects of Humate on Acute Inflammatory Response

Male Sprague Dawley rats weighing approximately 50 g were purchased from Harlan U.S. and housed in wire cages in the animal facility at Mercer University School of Pharmacy. The animals were given a short period of time to acclimate to the new environment and received powdered rat chow from Purina and water ad libitum. At the beginning of the experimental period, insoluble, granular Menefee Humate® was mixed with the powdered rat chow and placed in feeders. Rats received chow with either 0.1%, 0.5% or 1.0% insoluble, granular Menefee Humate® by weight. After 54 days of receiving humate in their food, the animals were injected in the subplantar region of the left hind paw with carrageenan (2%; 0.5 mg in 0.05 ml of saline). This substance produces an acute inflammation in the infected paw that increases over time and reaches a maximum approximately three hours post-injection. The contralateral paw received only saline and served as the negative control.

The paw volumes were measured plethysmographically by displacement of mercury three hours post-injection of the carrageenan. The volume of the negative control paw was subtracted from the volume of the carrageenan-injected paw to determine the degree of inflammation present. The average volume of edema obtained from the Menefee Humate®-treated animals was divided by the average volume of edema from the control animals (carageenan only, no humate) and the quotient (multiplied by 100) subtracted from 100 to obtain the percent inhibition of edema produced by Menefee Humate®.

Figure 1:
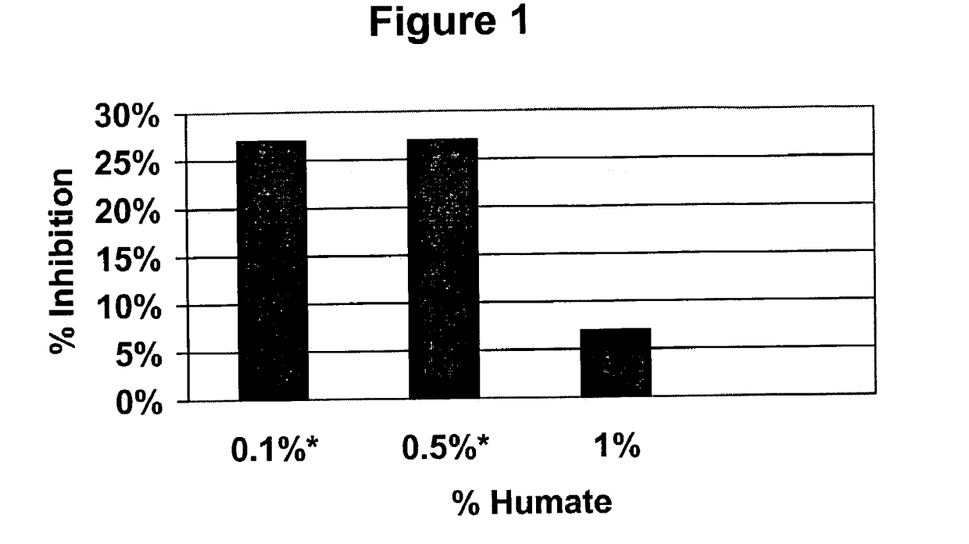
FIG. 1 depicts the inhibitory effects of orally administered insoluble, granular Menefee Humate® on carrageenan-induced edema in rats. Percent inhibition reflects inhibition of swelling in an edemic paw as compared to a non-edemic paw. Solution percentages represent weight percentage of humate in powder suspension with feed mix.

The effect of insoluble, granular Menefee Humate® on carrageenan-induced edema is shown in FIG. 1. The 0.1% and the 0.5% concentrations of humate produced a similar and statistically significant inhibition of hind paw inflammation. The inhibition was approximately 27% (P<0.05). The higher concentration of humate did not affect the inflammatory process.

In the 0.1% group, there was one animal whose response to inflammation did not appear to be typical of animals of that group. If that animal is eliminated from the results, there was actually a 48% inhibition of carrageenan-induced edema. Therefore, it appears that at certain concentrations beginning at approximately 0.1% by weight of food, orally administered insoluble, granular Menefee Humate® inhibits acute inflammation. This effect does not persist however, at higher concentrations of humate, beginning at approximately 1.0% by weight of food.

Example 3

Effect of Insoluble, Granular Menefee Humate® on Anti-Inflammatory Activity of Indomethacin Male Sprague Dawley rats weighing approximately 50 g were purchased from Harlan U.S. and housed in wire cages in the animal facility at Mercer University School of Pharmacy. The animals were given a short period of time to acclimate to the new environment and received powdered rat chow from Purina and water ad libitum. At the beginning of the experimental period, the rats were divided into six groups of eight each. Control and indomethacin only groups received only powdered rat chow for the entire length of the experiment. For the four other groups, insoluble granular Menefee Humate® was mixed with the powdered rat chow and placed in feeders. Rats received chow with either 0.1%, 0.5% or 1.0% insoluble, granular Menefee Humate® by weight. After 37 days of receiving humate in their food, the animals weighed approximately 278 g, which in an appropriate size for inducing inflammation. An amount of indomethacin sufficient to achieve 50% inhibition of carrageenan-induced edema (3 mg/kg) was administered to the indomethacin only group and to the 0.1% humate plus indomethacin group. The indomethacin was administered subcutaneously 30 minutes before the administration of carageenan. The rats were then injected in one hind paw with carrageenan (2%). After three hours, the hind paws were measured by mercury displacement.

Figure 2:
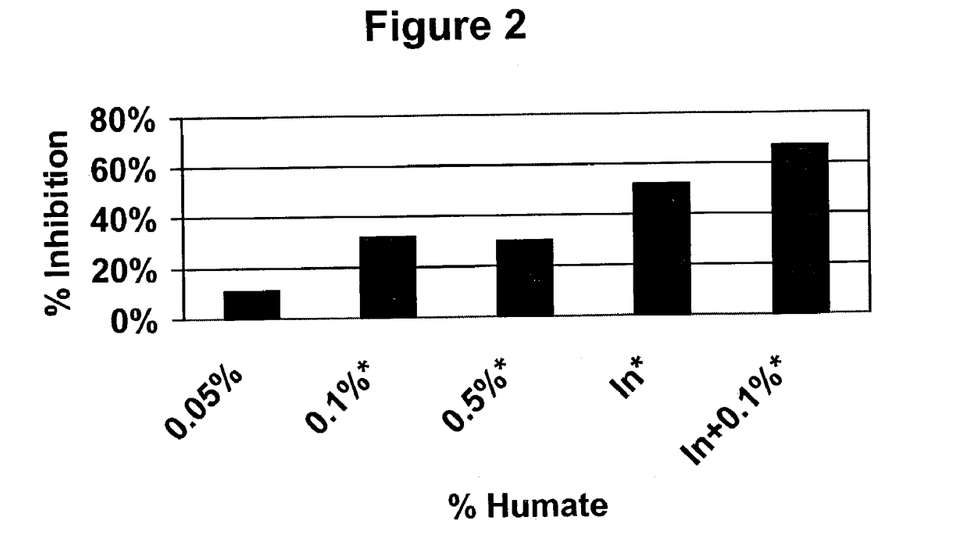
FIG. 2 depicts the inhibitory effects of orally administered insoluble, granular Menefee Humate®, indomethacin, and Menefee Humate® plus indomethacin on carrageenan-induced edema in rats. Percent inhibition reflects swelling in an edemic paw as compared to a non-edemic paw. Solution percentages represent weight percentage of humate in powder suspension with feed mix.

The results of this experiment are shown in FIG. 2. As in Example 2, the animals receiving 0.1% or 0.5% humate exhibited significant inhibition of inflammation (approximately 30%, P<0.05). That receiving only 0.05% humate exhibited only around a 10% inhibition of inflammation, indicating that this dose was too low to have a significant effect on carrageenan-induced edema. Those animals receiving only indomethacin exhibited around a 50% inhibition of edema, as expected (P<0.05).

Surprisingly, the animals that received both indomethacin and 0.1% concentration of humate exhibited a 66.8% inhibition of carrageenan-induced edema (P<0.05). This represents a 28% increase in the anti-inflammatory activity as compared to indomethacin alone. These results suggest that a combination of indomethacin or another anti-inflammatory agent with insoluble, granular Menefee Humate® or another humate may allow the administration of lower amounts of the non-humate anti-inflammatory compound. Given the toxicity and side-effects of many known anti-inflammatory compounds (which are much more dangerous or discomforting than any known side-effects of humate), this capacity to lower the dose of such compounds required to treat inflammation may greatly benefit both human and animal patients.

The basis for this increase in the effectiveness of indomethacin may be due to a synergistic combination of the anti-inflammatory effects of humate and those of indomethacin. However, given the tendency of humate to bind to other molecules and transport them across lipid membranes, it is also possible that the humate serves as a carrier of the indomethacin, allowing it to reach target areas more readily.

Example 4

Effects of Menefee Humate® on Chronic, Immunologically-Induced Inflammatory Response Male Sprague Dawley rats weighing approximately 50 g were purchased from Harlan U.S. and housed in wire cages in the animal facility at Mercer University School of Pharmacy. The animals were given a short period of time to acclimate to the new environment and received powdered rat chow from Purina and water ad libitum. At the beginning of the experimental period, the rats were divided into six groups of eight each. Negative and positive control groups received only powdered rat chow for the entire length of the experiment. For the four other groups, insoluble, granular Menefee Humate® was mixed with the powdered rat chow and placed in feeders. Rats received chow with either 0.1%, 0.5% or 1.0% insoluble, granular Menefee Humate® by weight. All rats remained on their assigned diets for 17 days prior to *mycobacterium* administration and for 21 days after the administration.

When the animals reached a body weight known to allow the greatest amount of inflammation (around 180 g), a heat-killed and dried *Mycobacterium butyricum* (10 mg) suspended in light mineral oil was injected into the base of the tail of all animals except the negative control animals. The negative control group received an injection of mineral oil only.

The *Mycobacterium* Wax D fraction induces a cellular immune response with the first signs of inflammation appearing approximately 12 to 15 days post-injection. At that time, an inflammatory response was observed in all but the negative control animals. The inflammatory response occurred in both hind paws, both fore paws and the ears of the animals. The inflammation of the hind paws as measured plesthmographically by displacement of mercury was measured at 15 and 21 days post-injection. The degree of inflammation in the forepaws and ears as well as the degree of hind paw ankylosis was determined using a grading system know to the art as the arthrogram score.

Figure 3A:
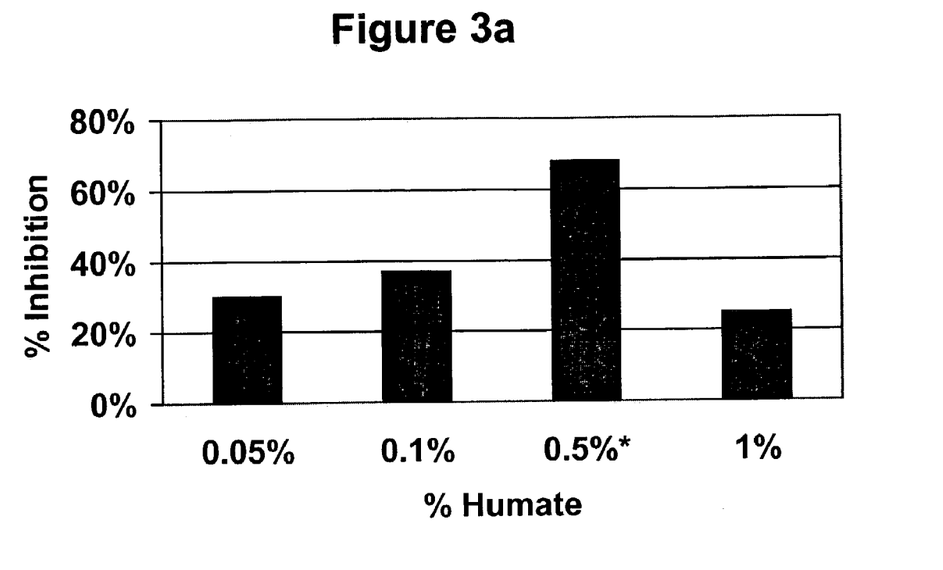
FIG. 3a depicts the effect of Menefee Humate® on % change in arthrogram score after 15 days of humate administration.
Figure 3B:
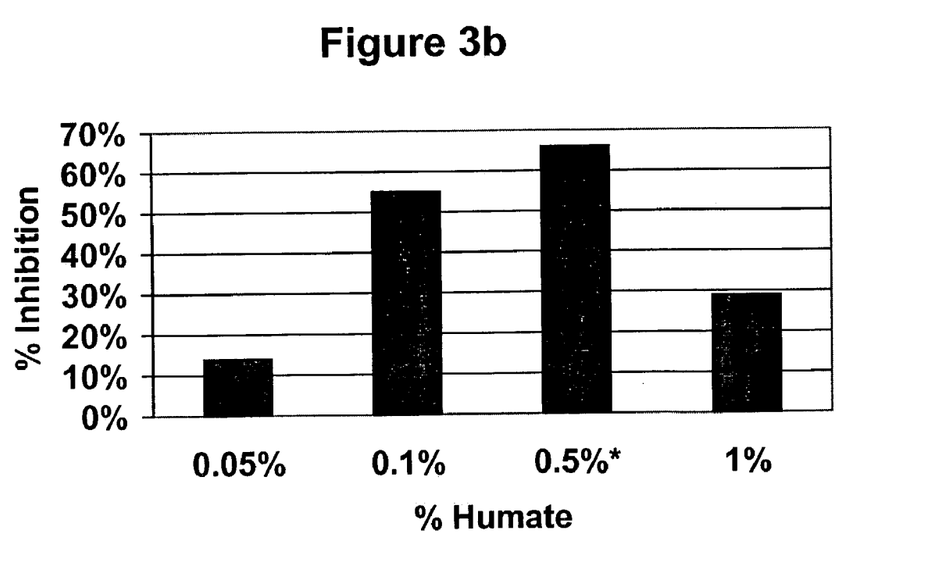
FIG. 3b depicts the % change effect of Menefee Humate® on right hind paw volume after 15 days of administration.
Figure 3C:
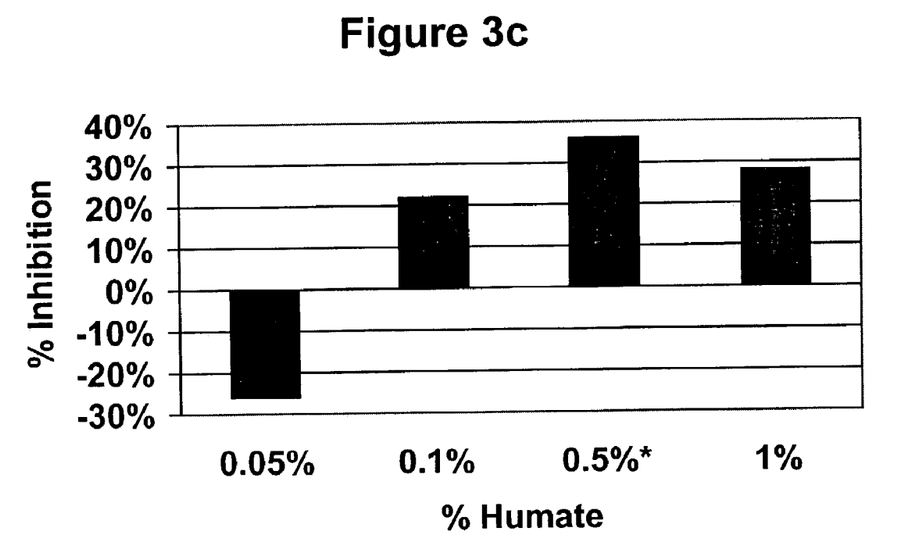
FIG. 3c depicts the % change effect of Menefee Humate® on left hind paw volume after 15 days of administration.
Figure 4A:
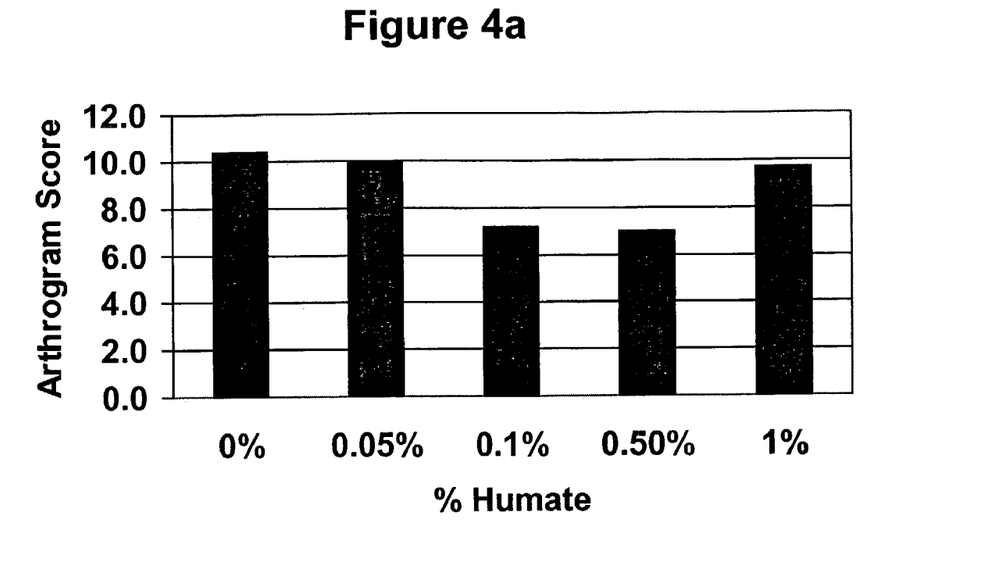
FIG. 4a depicts the effect of Menefee Humate® on arthrogram score after 21 days of humate administration.
Figure 4B:
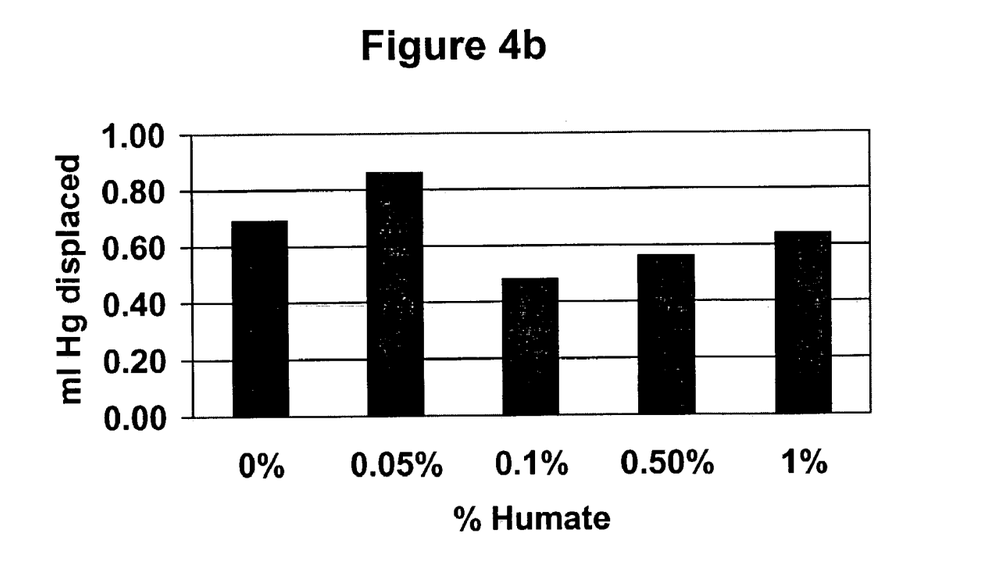
FIG. 4b depicts the effect of Menefee Humate® on right hind paw volume in mm of Hg displaced after 21 days of administration.
Figure 4C:
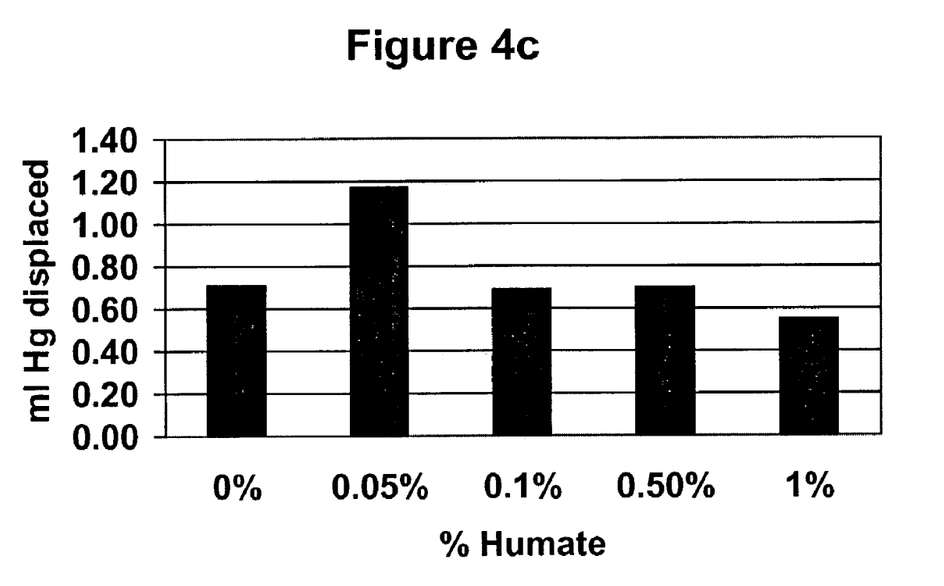
FIG. 4c depicts the effect of Menefee Humate® on left hind paw volume in mm Hg displaced after 21 days of administration.

The effect of insoluble, granular Menefee Humate® on arthritis in rats 15 days after injection is shown in FIGS. 3a, b and c. The effects of humate on inflammation 21 days after injection are shown in FIGS. 4a, b and c. Arthrogram scores were obtained by visually grading the following: fore paws, redness and swelling; ear, redness and/or nodular lesions; hind paws, ankylosis; and tail, ankylosis and/or nodules. The scoring system ranged from 0 to 2+, where 0 indicates no indications, 1+ indicates moderate indications and 2+ indicates severe indications. A maximal score of 18 could this be obtained. The average score obtained by the drug-treated group was divided by the average score obtained by the arthritic control group time 100. This number was subtracted from 100 to obtain the percent inhibition caused by the Menefee Humate®.

To obtain the percent inhibition of adjuvant arthritis produced by the Menefee Humate®, the following calculations were made: the average hind paw volume obtained for each paw of the negative control animals (no adjuvant, only mineral oil) was subtracted from the average hind paw volume obtained for each paw of the positive control animals (animals received *mycobacterium*). This volume represents the true inflammation produced in the controls. The same procedure was performed on the Menefee Humate®-treated animals to obtain the inflammation produced in these animals. The effect of the inflammation produced by the Menefee Humate® was then obtained by dividing the inflammation obtained in the Menefee Humate®-treated group by the inflammation obtained in the positive control group times 100. The number was then subtracted from 100 to obtain the % inhibition produced by the Menefee Humate®.

The 0.5% concentration of the insoluble, granular Menefee Humate® produced a statistically significant inhibition of the arthrogram score (FIG. 3a) and right hind paw swelling (FIG. 3b) on the 15th day after *Mycobacterium* injection (P<0.05 for 0.5% concentration in both). Although some inhibition was also seen in the left paw, it was not statically significant (FIG. 3c). The 0.05%, 0.1% and 1% concentrations of humate did not produce a significant inhibitory effect on either the arthrogram score or swelling in the left or right hind paw. When the effects of insoluble, granular Menefee Humate® on chronic inflammation were evaluated again at 21 days post-injection so statistically significant inhibition of inflammation was seen.

This suggests that Menefee Humate®, when ingested orally at a concentration of approximately 0.5% by food weight prior to and during onset of chronic inflammation, has an inhibitory effect on chronic inflammation. However, such inhibitory effect is not maintained for the long-term. Nevertheless, these results indicate that humate may serve a purpose in delaying the onset of debilitating effects of chronic inflammatory diseases, such as arthritis. Humate may also present a viable alternative to stronger medications that may have harmful side effects during the early stages of some chronic inflammations.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An anti-inflammatory composition comprising:
   MENEFEE HUMATE®;
   at least one additional anti-inflammatory agent; and
   a pharmaceutically acceptable carrier.

2. The composition of claim 1, wherein the humate is prehistoric humate.

3. The composition of claim 2, wherein the humate is derived from the Menefee Geological Formation in New Mexico.

4. The composition of claim 1, wherein the humate comprises at least 50% humic acids.

5. The composition of claim 1, wherein the composition is for oral or topical administration and the humate is insoluble, granular humate.

6. The composition of claim 1, wherein the composition is for injection administration and the humate is soluble.

7. The composition of claim 1, wherein the humate comprises between approximately 0.1% and 1.0% by weight of the total weight of the composition.

8. The composition of claim 7, wherein the humate comprises approximately 0.1–0.5% by weight of the total weight of the composition.

9. The composition of claim 1, wherein at least one additional anti-inflammatory agent is a nonsteroidal anti-inflammatory drug.

10. The composition of claim 9, wherein the nonsteroidal anti-inflammatory drug is an indole derivative.

11. The composition of claim 10, wherein the nonsteroidal anti-inflammatory drug is indomethacin.

12. A method of reducing inflammation in a tissue of an animal comprising:
    supplying a composition containing MENEFEE HUMATE® to the tissue through oral, topical or injection administration; and
    supplying at least one additional anti-inflammatory agent to the tissue through oral, topical or injection administration.

13. The method of claim 12, wherein the humate is supplied orally and constitutes approximately 0.1 to 0.5% by weight of the total food consumed by the animal.

14. The method of claim 12, wherein at least one additional anti-inflammatory agent is supplied in the composition containing humate.

15. The method of claim 12, wherein the at least one additional anti-inflammatory agent is supplied in a separate composition from that containing humate.

16. The method of claim 15, wherein the at least one additional anti-inflammatory agent supplied in a separate composition is supplied approximately contemporaneously with the composition containing humate using the same type of administration.

17. The method of claim 12, wherein the dosage of the at least one additional anti-inflammatory agent is reduced as compared to an appropriate dosage in the absence of humate.

18. The method of claim 13, wherein the humate acts as a carrier to facilitate transport of the second anti-inflammatory agent to targets of activity of the second anti-inflammatory agent.

19. The method of claim 12, wherein the composition containing humate is supplied orally and wherein humate constitutes approximately 0.1–0.5% by total weight of an animal's food intake and the at least one additional anti-inflammatory composition is indomethacin administered in the amount of approximately 3 mg/kg animal.

20. The method of claim 12, wherein the animal is a human.

21. The method of claim 12, wherein the inflammation is acute.

22. The method of claim 12, wherein the inflammation is chronic.

23. The method of claim 22, wherein the inflammation is a result of arthritis.

* * * * *